US00PP25067P2

(12) United States Plant Patent
Sidhu

(10) Patent No.: US PP25,067 P2
(45) Date of Patent: Nov. 18, 2014

(54) ***VACCINIUM* PLANT NAMED 'VACSID1'**

(50) Latin Name: *Vaccinium ovatum*
Varietal Denomination: Vacsid1

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 146 days.

(21) Appl. No.: 13/815,067

(22) Filed: Jan. 29, 2013

(51) Int. Cl.
*A01H 5/00* (2006.01)

(52) U.S. Cl.
USPC ..... Plt./157; Plt./156

(58) Field of Classification Search
USPC ..... Plt./156, 157
See application file for complete search history.

*Primary Examiner* — Susan McCormick Ewoldt
(74) *Attorney, Agent, or Firm* — Penny J. Aguirre

(57) ABSTRACT

A new cultivar of *Vaccinium*, 'Vacsid1', that is characterized by its compact plant habit with sturdy stems, and its new foliage growth that is bright red in color.

3 Drawing Sheets

Botanical classification: *Vaccinium ovatum.*
Cultivar designation: 'Vacsid1'.

BACKGROUND OF THE INVENTION

The present invention relates to a new and distinct cultivar of *Vaccinium ovatum*, and will be referred to hereafter by its cultivar name, 'Vacsid1'. 'Vacsid1' is a new cultivar of Evergreen huckleberry is grown for use as a landscape shrub.

The new cultivar was discovered by the Inventor in 2006 as a naturally occurring branch mutation of *Vaccinium ovatum* 'Thunderbird' (not patented) that was growing in a container in his nursery in Mission, B.C., Canada.

Asexual propagation of the new cultivar was first accomplished by the Inventor by stem cuttings in Mission, B.C., Canada in 2007. Asexual propagation by stem cuttings and in vitro propagation has determined that the characteristics of this cultivar are stable and are reproduced true to type in successive generations.

SUMMARY OF THE INVENTION

The following traits have been repeatedly observed and represent the characteristics of the new cultivar, which in combination distinguish 'Vacsid1' as a new and distinct cultivar of *Vaccinium.*

1. 'Vacsid1' exhibits a compact plant habit with sturdy stems.
2. 'Vacsid1' exhibits new foliage growth that is bright red in color.

'Thunderbird', the parent plant of 'Vacsid1', differs from 'Vacsid1' in that the plant habit is not compact and the branches are weaker. 'Vacsid1' can also be compared to the cultivar 'Wunderlich' (not patented) and 'Blue Madonna' (not patented). 'Wunderlich' differs from 'Vacsid1' in being a large leaved form, in being taller in height and in having a more vigorous growth habit. 'Blue Madonna' differs in having mature leaves that are chalky blue in color.

BRIEF DESCRIPTION OF THE DRAWINGS

The accompanying colored photographs illustrate the overall appearance and distinct characteristics of the new *Vaccinium*. The photographs were taken of a plant about three years in age as grown outdoors in a two-gallon container in Mission, B.C., Canada.

The photograph in FIG. 1 provides a view of the plant habit of 'Vacsid1'.

Figure 1:
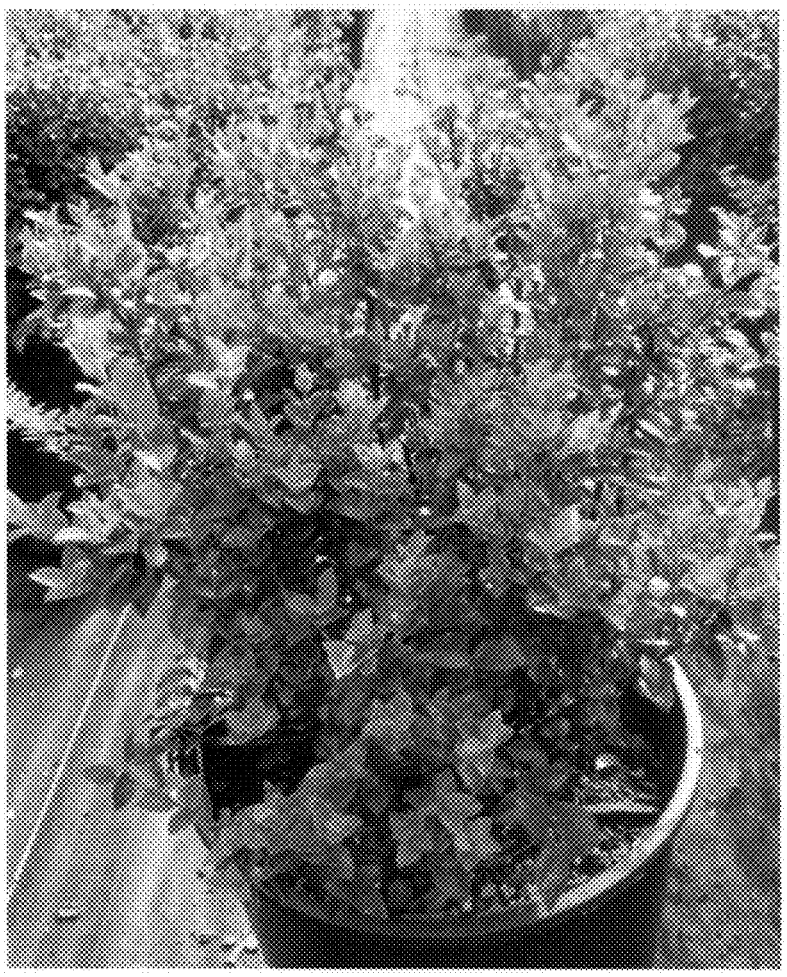
Figure 2:
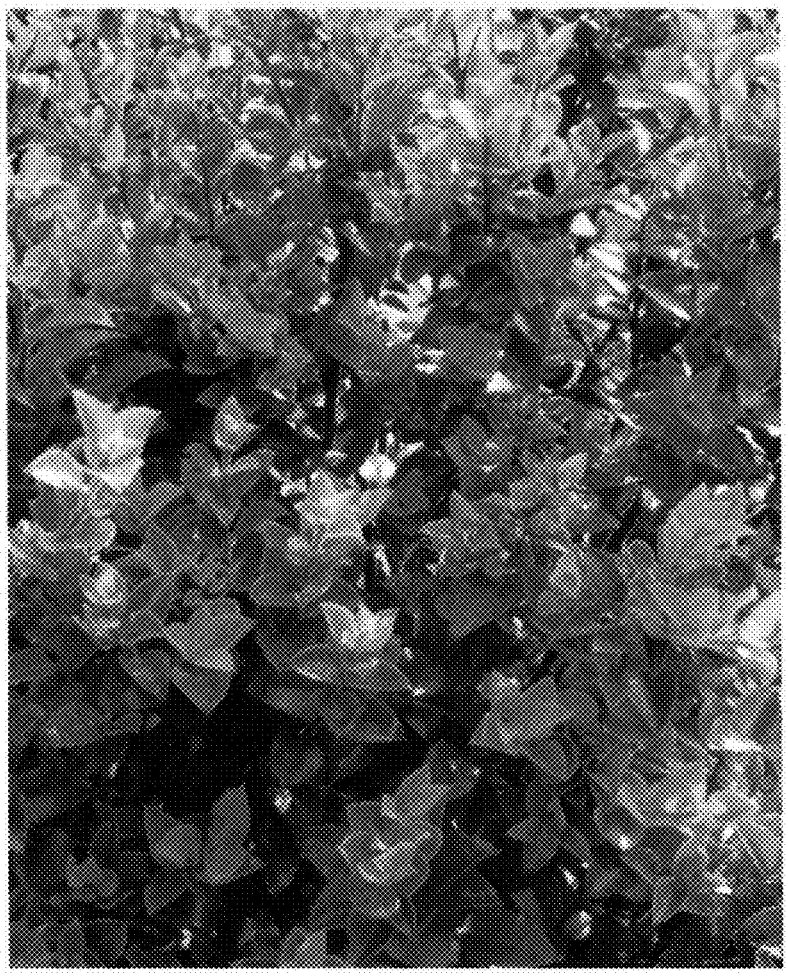

The photograph in FIG. 2 provides a close-up view of the foliage of 'Vacsid1'.

Figure 3:
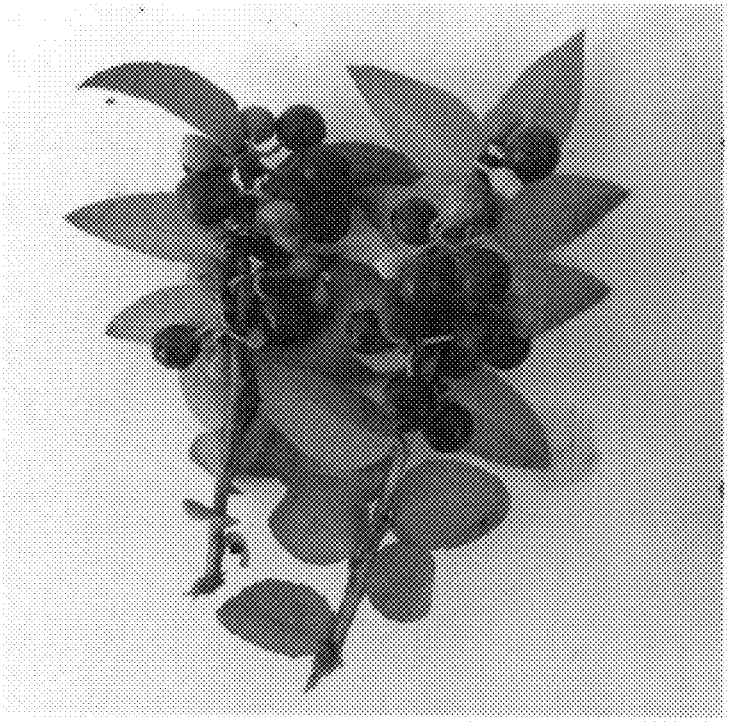

The photograph in FIG. 3 provides a close-up view of maturing and mature fruit of 'Vacsid1'.

Figure 4:
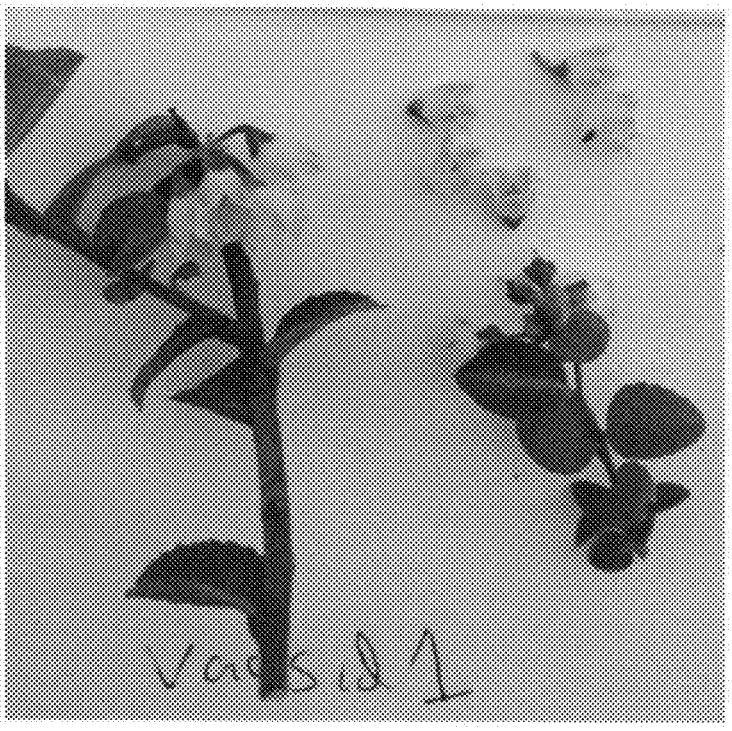

The photograph in FIG. 4 provides a close-up view of an inflorescence of 'Vacsid1'.

The colors in the photographs may differ slightly from the color values cited in the detailed botanical description, which accurately describe the colors of the new *Vaccinium.*

DETAILED BOTANICAL DESCRIPTION OF THE PLANT

The following is a detailed description of two year-old plants of the new cultivar grown outdoors in 1-gallon containers in Mission, B.C., Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Blooming period.*—About 6 weeks in spring in Mission, B.C., Canada.

*Plant type.*—Evergreen shrub.

*Plant habit.*—Compact, dense, broadly upright spreading.

*Height and spread.*—Reaches about 76 cm in height and 106 cm in width.

*Hardiness.*—Hardy to at least U.S.D.A. Zone 7 in Canada.

*Disease resistance.*—No particular resistance to diseases has been observed.

*Root description.*—Fibrous.

*Growth rate.*—Slow to moderate.

*Propagation.*—Stem cuttings and tissue culture.

Stem description:

*Stem size.*—Lateral branches are an average of 14 cm in length and 1.5 mm in width, secondary branches; an average of 10 cm in length and 1 cm in width.

*Stem shape.*—Round.

*Stem color.*—Young shoots; 145A, later turning 34A, mature stems; 144A.

*Stem surface.*—Young stems; slightly glossy, mature stems; slightly glossy and moderately covered with wooly hairs 0.5 mm in length and 45A in color.

*Stem strength.*—Moderately strong.

*Internode length.*—Average of 3 mm.

*Branching habit.*—An average of 17 lateral branches from the base, with 0 to 5 secondary branches.

*Branching aspect.*—Lateral and secondary branches; upright to an angle of 45°.

Foliage description:

*Leaf shape.*—Ovate.

*Leaf division.*—Simple.

*Leaf base.*—Cordate.

*Leaf apex.*—Broadly acute.

*Leaf venation.*—Pinnate.

*Leaf margins.*—Entire.

*Leaf attachment.*—Sessile.

*Leaf arrangement.*—Alternate.

*Leaf surface.*—Smooth, moderately glossy and slightly rugose on upper and lower surface.

*Leaf color.*—Upper surface new foliage; 137A and strongly suffused with 179A, lower surface new foliage; 138A and some suffusion of 179A, maturing foliage upper surface; 144B with a thin margin of 179A, maturing foliage lower surface; 138A, mature foliage upper surface; N137B, mature lower surface foliage; 146A.

*Leaf number.*—Average of 24 per lateral branch.

*Leaf size.*—Average of 7 mm in length and 4 mm in width.

*Leaf aspect.*—Held upward at about a 45° angle.

*Leaf fragrance.*—None.

*Leaf veins.*—Upper and lower surfaces same color as leaf color.

*Petioles.*—Average of 2 mm in length and 1 mm in width, upper and lower surfaces 144A in color.

Inflorescence description:

*Inflorescence.*—Pendulous terminal raceme of single flowers.

*Lastingness of inflorescence.*—Average of 7 to 10 days.

*Pedicels.*—Round in shape, an average of 5 mm in length and 0.5 mm in width, 144A in color, smooth surface.

*Peduncles.*—Round in shape, an average of 2.5 cm in length and 0.5 mm in width, a blend between 144A and 199B in color, surface moderately covered with wooly hairs 0.5 mm in length and 45A in color.

*Flowers.*—Campanulate in shape, an average of 10 flowers per raceme.

*Flower buds.*—Oval in shape, an average of 5 mm in length and 2.5 mm in width, color a blend between 73A and 72A in color.

*Flower size.*—Average of 8 mm in length and 5 mm in width.

*Sepals.*—5, ovate in shape, acute apex, fused base, an average of 3 mm in width and 4 mm in length, upper and lower surface 138A with tips 187B in color, margins entire.

*Petals.*—5, ovate in shape, acute apex, fused base, an average of 7 mm in length and 3 mm in width, upper and lower surface 69A to 69B with longitudinal stripes 72D in color, upper and lower surface smooth and glabrous, margins entire.

Reproductive organs:

*Gynoecium.*—1 pistil, an average of 6 mm in length; style is 151C in color and 5 mm in length, stigma 1 mm in diameter, ovary; 151C in color, 2 mm in length and width.

*Androcoecium.*—10 stamens, 6 mm in length and 0.5 mm in width, filament; an average of 5.5 mm in length, 0.5 mm in width, and 9A in color; dorsifixed anthers, an average of 1 mm in length and width and 9A in color, pollen is moderate in quantity and 9A in color.

Fruit description:

*Fruit number.*—12 fruits per branch 10 cm long.

*Fruit use.*—Not grown for fruit production.

*Fruit bearing season.*—Mid to late in Mission, B.C., Canada.

*Fruit size.*—Medium to large sized fruit, an average of 4 mm in diameter and height.

*Fruit shape.*—Globose.

*Persistence of calyx.*—Not persistent.

*Surface.*—Glossy, smooth, glabrous.

*Skin color.*—Immature 138B, maturing a blend between 93A, 138B and 181A, mature a blend between 95A and 103A.

*Color of flesh.*—A blend between 194A to 194C and 160A.

*Seed.*—Oblong to oval in shape, 30 per fruit, <1 mm in length and width, 171A to 171B in color.

It is claimed:

1. A new and distinct cultivar of *Vaccinium* plant named 'Vacsid1' as herein illustrated and described.

* * * * *